United States Patent [19]

Goe

[11] Patent Number: 5,061,805

[45] Date of Patent: Oct. 29, 1991

[54] PROCESS FOR PREPARING 2-METHYL-3,5-DIALKYLPYRIDINES BY DEALKYLATION WITH SULFUR

[75] Inventor: Gerald L. Goe, Greenwood, Ind.

[73] Assignee: Reilly Industries, Inc., Indianapolis, Ind.

[21] Appl. No.: 565,957

[22] Filed: Aug. 10, 1990

[51] Int. Cl.$^5$ .................. C07D 213/127; C07D 213/16
[52] U.S. Cl. ..................................... 546/349; 546/251
[58] Field of Search ................................ 546/251, 349

[56] References Cited

U.S. PATENT DOCUMENTS

| | | | |
|---|---|---|---|
| 4,255,431 | 3/1981 | Junggren et al. | 514/338 |
| 4,337,257 | 6/1982 | Junggren et al. | 514/338 |
| 4,658,032 | 4/1987 | Yamaji | 546/349 |

OTHER PUBLICATIONS

C. R. Adams & J. Falbe, *Brennstoff Chem.*, 47, 184–187 (1966).

*Primary Examiner*—Alan L. Rotman
*Attorney, Agent, or Firm*—Woodard, Emhardt, Naughton, Moriarty & McNett

[57] ABSTRACT

A process for dealkylating the 2-position on a trisubstituted pyridine derivative having the formula

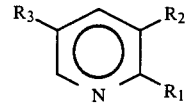

where $R_1$ is a straight chain alkyl group from about $C_2$–$C_5$ and where $R_2$ and $R_3$ are alkyl, aryl or aralkyl groups up to about $C_{10}$, comprising the step of reacting said pyridine derivative at reflux with excess sulfur. Of particular note is the preparation of 2,3,5-trimethylpyridine including the initial preparation of its 2-ethyl precursor by the Chichibabin reaction of propionaldehyde and ammonia.

7 Claims, No Drawings

PROCESS FOR PREPARING 2-METHYL-3,5-DIALKYLPYRIDINES BY DEALKYLATION WITH SULFUR

BACKGROUND OF THE INVENTION

This invention relates generally to the field of pyridine chemistry, and, more particularly to an improved process for preparing 2-methyl-3,5-dialkylpyridine derivatives.

Pyridine, with its characteristic aromatic ring structure, is the parent to a large number of substituted homologues and derivatives having uses in valuable industrial, pharmaceutical and agricultural chemicals. One such derivative is 2,3,5-trimethylpyridine, which is also known by the name 2,3,5-collidine.

For example, the compound 2,3,5-trimethylpyridine has recently proven valuable as a key intermediate for the synthesis of a highly-substituted pyridine derivative known as omeprazole, which has been accorded much medical and commercial interest because it and a family of related compounds have been found useful as gastric secretion inhibitors for treating ulcers and related diseases. U.S. Pat. No. 4,255,431, and U.S Pat. No. 4,337,257. However, while being an important raw material in the pharmaceutical world, 2,3,5-trimethylpyridine has been obtained previously only with much difficulty and expense.

For instance, one known process for preparing 2,3,5-trimethylpyridine is disclosed in U.S. Pat. No. 4,658,032, and comprises reacting 3,5-dimethylpyridine with a lower aliphatic alcohol ($C_{1-4}$) in the presence of a Raney cobalt or nickel catalyst. However, the reaction described therein requires reaction pressures preferably in the range of 10 to 60 kg/cm$^2$ and temperatures preferably in the range of 230°-270° C. Such pressures and temperatures are both difficult and expensive to achieve in industry. Additionally, the catalysts used are expensive and difficult to handle, particularly when commercial scale production is contemplated.

U.S. Pat. No. 4,658,032 in the background section also generally discusses three other known routes to 2,3,5-trimethylpyridine.

First, this compound may be obtained by separating and purifying 2,3,5-trimethylpyridine from shale oil contained in pitchstone or the like. However, this process is industrially disadvantageous because the amount of 2,3,5-trimethylpyridine present in the raw shale oil material is very small, and thus large quantities must be used to produce quantities of 2,3,5-trimethylpyridine sufficient to meet needs on an industrial level.

Second, 2,3,5-trimethylpyridine can be synthesized by bringing ammonia into contact with propionaldehyde and acetaldehyde in the presence of alumina at a reaction temperature of 340° C. However, this process is unsatisfactory on an industrial scale because the yield of 2,3,5-trimethylpyridine is generally low.

Third, 2,3,5-trimethylpyridine may be produced by reacting 3,5-dimethylpyridine with methyllithium. This process, however, is disadvantageous in that methyllithium is very expensive and the use of this organic alkali metal compound, which is subject to decomposition by water or oxygen, is thought to be indispensable, and thus special care must be taken in handling this compound.

In light of the short comings of these previously known methods for preparing the compound 2,3,5-trimethylpyridine, there exists a need for an improved method for preparing the same which provides a good yield and does not require the use of disadvantageous temperatures or pressures, or of expensive materials or catalysts. The applicant's invention addresses this need.

SUMMARY OF THE INVENTION

The applicant has now made the significant and unexpected discovery that 2,3,5-trimethylpyridine may be prepared simply by reacting 2-ethyl-3,5-dimethylpyridine with sulfur. In a like fashion, 2-ethyl-3,5-dialkylpyridine derivatives having alkyl groups larger than methyl located at the 3- and 5- positions of the pyridine ring also dealkylate at the 2- position upon reacting with sulfur to form their 2-methyl-3,5-dialkylpyridine counterparts which are also recognized to have valuable intermediary and other properties.

Accordingly, one preferred embodiment of the present invention involves a process comprising reacting 2-ethyl-3,5-dialkylpyridine derivatives with sulfur to form their 2-methyl-3,5-dialkylpyridine derivative counterparts. In a more preferred mode of practicing this embodiment, 2,3,5-trimethylpyridine may be formed by reacting 2-ethyl-3,5-dimethylpyridine with sulfur.

One object of the present invention is to provide a simple method of preparing 2-methyl-3,5-dialkylpyridine derivatives.

Another object of the present invention is to provide a method for preparing 2,3,5-trimethylpyridine which does not involve the disadvantages of known prior art methods.

Another object of the present invention is to provide a method for preparing 2,3,5-trimethylpyridine which includes the step of reacting 2-ethyl-3,5-dimethylpyridine with sulfur.

Related objects and advantages of the present invention will be apparent from the description that follows.

DESCRIPTION OF THE PREFERRED EMBODIMENT

For the purposes of promoting an understanding of the principles of the invention, reference will now be made to preferred embodiments of applicant's work and specific language will be used to describe the same. It will nevertheless be understood that no limitation of the scope of the invention is thereby intended, such alterations and further modifications, and such further applications of the principles of the invention therein being contemplated as would normally occur to one skilled in the art to which the invention relates.

In accordance with the above discussion, one embodiment of the invention comprises a process for dealkylating the 2- position on a trisubstituted pyridine derivative having the general formula

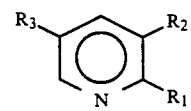

where $R_1$ is a straight chain alkyl group from about $C_2$-$C_5$ and where $R_2$ and $R_3$ are alkyl, aryl or aralkyl groups up to about $C_{10}$. This process comprises the step of reacting this pyridine derivative under heat with excess sulfur to accomplish the functionalization of the 2-alkyl group on the ring apparently through migration of the functionality along the chain and loss of the terminal carbon possibly through a carbon disulfide compound. The result is the effective shortening, or "dealkylation" as the term is understood and used herein, of the alkyl group at the 2- position to a lower alkyl component.

In this regard, one preferred aspect of the above embodiment comprises a process for preparing 2,3,5-trimethylpyridine, also known as 2,3,5-collidine, without the difficulty or inefficiency of previously known methods. Broadly defined, this process comprises the single step of reacting 2-ethyl-3,5-dimethylpyridine, also known as α-parvoline, under heat with sulfur to selectively dealkylate the 2-ethyl group thereby forming the desired 2,3,5-trimethylpyridine compound.

As to specific procedures and conditions of applicant's reactions to date, they have been conducted by mixing amounts of the selected 2-ethyl-3,5-dimethylpyridine or other precursor material with a sulfur source such as elemental sulfur and then heating this mixture under standard reflux for periods of time ranging from 4 to 30 hours. The preferred period of time to date has been about 4 to 8 hours. Experimentation has also shown that the preferred mixture is in a mole ratio of at least about 3:1 sulfur to 2-ethyl-3,5-dimethylpyridine or other precursor in order to maximize production and yield of 2,3,5-trimethylpyridine or other corresponding product.

To date, the applicant has flash distilled the reaction mixture upon completion of the reflux, thus removing all liquid and leaving behind unreacted sulfur and tar. The removed liquid has then been analyzed by gas chromatography, which has indicated excellent yields of 2,3,5-trimethylpyridine or other dealkylated pyridine derivatives in the range of at least about 60% to 70% of theory.

Additionally, in the applicant's reactions to date, a further aspect has been to first generate the preferred 2-ethyl-3,5-dimethylpyridine used by carrying out a Chichibabin synthesis reaction using propionaldehyde and ammonia. More specifically the method described by C. R. Adams and J. Falbe in *Brennstoff Chem.*, 47, 184–187 (1966) has been used. The method of Adams and Falbe involves treating saturated aldehydes with $NH_3$ over fixed-bed catalysts. This is done at atmospheric pressure and at a temperature of 350° C., for about a 2 second contact time, to give the corresponding 2,3,5-trialkylpyridine derivative. Adams and Falbe disclosed various catalysts for the reaction including $CoAl_2O_4$, $Al_2O_3$, $Cr_2O_3/Al_2O_3$, Cu chromite, and $Co_3Al_2(PO_4)_3$, with the latter being preferred by the two authors. Using this method with $Co_3Al_2(PO_4)_3$ as the catalyst, Adams and Falbe reported a 65% yield of 2-ethyl-3,5-dimethylpyridine from the reaction of propionaldehyde with ammonia.

In other preferred aspects of the above embodiment of the applicant's invention, other 2,3,5-trisubstituted pyridine derivatives are used which have longer straight chain alkyl groups at their 2- position up to at least about $C_5$ and further have larger alkyl, aryl or aralkyl groups at their 3- and 5- positions up to at least about $C_{10}$. These pyridine precursors functionally dealkylate at their 2- position to produce their lower alkyl counterparts under similar conditions upon reacting under heat and in the presence of excess sulfur both as described above. Because the alkyl groups at the 3- and 5- positions are not sensitive to oxidation and are unactivated or unaffected by the dealkylation, they remain intact throughout the reaction and would be expected to do so.

Similar reactions occur and would be expected where the 3- and 5- groups are propyl, butyl and other larger alkyl groups as well as aryl groups, including heterocylic aryls, and aralkyl groups.

In another aspect of the applicant's work to date, because the reaction generates hydrogen sulfide gas, it has been preferred to date to use an $H_2S$ trapping system, such as bubbling the waste gases from the reflux through a solution of sodium carbonate in water, to help alleviate the strong odor of the gas.

For the purpose of promoting a further understanding of the results of applicant's work to date and the scope and breadth of his invention as described and claimed herein, reference is now made to the specific examples which follow.

EXAMPLE 1

A mixture of 2-ethyl-3,5-dimethylpyridine (260 g), which had been prepared by the method of Adams and Falbe and elemental sulfur (210 g) was heated under reflux for 16.5 hr. The mixture was distilled once, without fractionation, to a temperature of 200° C. and the distillate was analyzed by gas chromatography to indicate a 67% yield of 2,3,5-trimethylpyridine based on 91% conversion of the 2-ethyl-3,5-dimethylpyridine charged. Fractional distillation of several reaction mixtures combined gave 2,3,5-trimethylpyridine of 95–97% purity, with the boiling point of 185°–187° C.

EXAMPLE 2

The procedure of Example 1 was used except that 244 grams of 2-ethyl-3,5-dimethylpyridine and 197 grams of sulfur were used, and the mixture was heated under reflux for 31 hours. The yield of 2,3,5-trimethylpyridine was 65% based on a 92% conversion of the 2-ethyl-3,5-dimethylpyridine charged.

EXAMPLE 3

The procedure of Example 1 was used except that 251 grams of 2-ethyl-3,5-dimethylpyridine and 203 grams of sulfur were used, and the mixture was heated under reflux for 8 hours. The yield of 2,3,5-trimethylpyridine was 66% based on a 92% conversion of the 2-ethyl-3,5-dimethylpyridine charged.

EXAMPLE 4

The procedure of Example 1 was used except that 246 grams of 2-ethyl-3,5-dimethylpyridine and 186 grams of sulfur were used, and the mixture was heated under reflux for 6 hours. The net yield of 2,3,5-trimethylpyridine was 78% based on an 89% conversion of the 2-ethyl-3,5-dimethylpyridine charged.

EXAMPLE 5

The procedure of Example 1 was used except that 327 grams of 2-ethyl-3,5-dimethylpyridine and 239 grams of sulfur were used, and the mixture was heated under reflux for 4 hours. A 68% conversion of the 2-ethyl-3,5-dimethylpyridine charged was demonstrated.

I claim:

1. A process for dealkylating the 2- position on a trisubstituted pyridine derivative having the formula

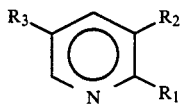

where $R_1$ is a straight chain alkyl group from about $C_2$–$C_5$ and where $R_2$ and $R_3$ are alkyl, aryl or aralkyl groups up to about $C_{10}$, comprising the step of reacting said pyridine derivative under heat with sulfur.

2. The process of claim 1 wherein $R_1$ is an ethyl group and $R_2$ and $R_3$ are methyl groups.

3. The process of claim 1 wherein said reacting is under reflux at a temperature of at least about 150° C.

4. The process of claim 3 wherein said reacting is with excess sulfur at a mole ratio of at least about 3:1 of sulfur to said trisubstituted pyridine precursor.

5. The process of claim 4 wherein said reacting is for a period of about 4–30 hours.

6. The process of claim 5 comprising the additional step of using an $H_2S$ absorption system to trap $H_2S$ gas evolved during said reacting.

7. A process for preparing 2,3,5-trimethylpyridine comprising the steps of initially preparing 2-ethyl-3,5-dimethylpyridine by the Chichibabin reaction of propionaldehyde and ammonia, followed by heating said 2-ethyl-3,5-dimethylpyridine at reflux with excess sulfur.

* * * * *